(12) United States Patent
Eck et al.

(10) Patent No.: US 9,717,683 B1
(45) Date of Patent: Aug. 1, 2017

(54) LOW-TEMPERATURE INHALATION ADMINISTRATION OF CANNABINOID ENTITIES

(71) Applicant: EP Pharma, LLC, Fall River, MA (US)

(72) Inventors: Charles Raymond Eck, Shrewsbury, MA (US); Christopher L. Pelloni, Newtown, PA (US)

(73) Assignee: EP PHARMA, LLC, Fall River, MA (US)

( * ) Notice: Subject to any disclaimer, the term of this patent is extended or adjusted under 35 U.S.C. 154(b) by 0 days.

(21) Appl. No.: 15/196,315

(22) Filed: Jun. 29, 2016

(51) Int. Cl.
| | |
|---|---|
| *A61K 31/05* | (2006.01) |
| *A61K 9/00* | (2006.01) |
| *A61K 9/12* | (2006.01) |
| *A61M 15/00* | (2006.01) |
| *A61M 11/04* | (2006.01) |

(52) U.S. Cl.
CPC .............. *A61K 9/008* (2013.01); *A61K 9/124* (2013.01); *A61K 31/05* (2013.01); *A61M 11/04* (2013.01); *A61M 15/009* (2013.01)

(58) Field of Classification Search
None
See application file for complete search history.

(56) References Cited

U.S. PATENT DOCUMENTS

| | | | |
|---|---|---|---|
| 6,509,005 B1 | 1/2003 | Peart et al. | |
| 6,713,048 B2 | 3/2004 | Peart et al. | |
| 7,726,310 B2 | 6/2010 | Andrus et al. | |
| 7,968,594 B2 | 6/2011 | Guy et al. | |
| 8,211,946 B2 | 7/2012 | Whittle | |
| 8,337,908 B2 | 12/2012 | Letzel | |
| 8,481,091 B2 | 7/2013 | Ross | |
| 8,512,767 B2 | 8/2013 | Ross | |
| 8,673,368 B2 | 3/2014 | Guy et al. | |
| 8,771,760 B2 | 7/2014 | Guy et al. | |
| 9,044,390 B1 | 6/2015 | Speier | |
| 9,205,063 B2 | 12/2015 | Guy et al. | |
| 2005/0061314 A1* | 3/2005 | Davies | A61K 9/008 128/200.23 |
| 2005/0079136 A1 | 4/2005 | Woolfe et al. | |
| 2005/0165088 A1* | 7/2005 | Whittle | A61K 31/05 514/454 |
| 2007/0072939 A1 | 3/2007 | Kupper | |
| 2008/0017191 A1 | 1/2008 | Davies et al. | |

(Continued)

FOREIGN PATENT DOCUMENTS

| | | |
|---|---|---|
| WO | 0024362 | 5/2000 |
| WO | 03006010 A1 | 1/2003 |

(Continued)

OTHER PUBLICATIONS

Fax (Draft Amendment, 3 NPLs) Received from Applicants' Attorney, Jun. 15, 2017, pp. 1-34.*

(Continued)

*Primary Examiner* — Aradhana Sasan
(74) *Attorney, Agent, or Firm* — Irving M Fishman

(57) ABSTRACT

A cannabinoid material as active agent containing formulation comprising the active agent, an HFA propellant, and optionally a co-solvent is disclosed. Also disclosed is an inhalation method of administration of the formulation without the use of heat greater than 50° C.

19 Claims, 1 Drawing Sheet

(56) References Cited

U.S. PATENT DOCUMENTS

| | | | |
|---|---|---|---|
| 2010/0317729 | A1 | 12/2010 | Guy et al. |
| 2015/0165030 | A1 | 6/2015 | Rossi |
| 2015/0203434 | A1 | 7/2015 | Flockhart |
| 2015/0231108 | A1 | 8/2015 | Hearn et al. |
| 2015/0297653 | A1 | 10/2015 | Speier |
| 2016/0151275 | A1 | 6/2016 | Shurtleff et al. |

FOREIGN PATENT DOCUMENTS

| | | | | |
|---|---|---|---|---|
| WO | 2004016277 | A2 | 2/2004 | |
| WO | 2015195711 | A2 | 12/2015 | |
| WO | 2015200049 | A1 | 12/2015 | |
| WO | WO 2015/198071 | A1 * | 12/2015 | ............. A61K 31/05 |

OTHER PUBLICATIONS

Administrator, Pure Analytics Blog; Acidic versus Activated Cannabinoids—Tips on How to Choose the Therapy Regimen that is Right for You; May 9, 2012; 3 pages.

Throckmorton; Cannabinol:Barriers to Research and Potential Medical Benefits; Jun. 24, 2015; (9 pages) http:/www.fda.gov/newsevents/testimony/ucm453989.htm.

Cannabinoid; https://en.wikipedia.org/wiki/Cannabinoid; Jul. 25, 2016; 15 pages.

Romano et al; Cannabis Oil: chemical evaluation of an upcoming cannabis-based medicine; Cannabinoids 2013; 1(1): 1-11.

Brenneisen; Chemistry and Analysis of Phytocannabinoids and Other Cannabis Constituents; Chapter 2 from Forensic Science and Medicine: Marijuana and the Cannabinoids, Edited by M.A.ElSohly (Humana Press Inc., Totowa, NJ 2007).

Scientists figure out how much pot is in a joint; http://www.newser.com/story/228246/scientists-determine-how-much-pot-is-in-a-joint.html; Jul. 18, 2016.

Public Information Report on Sativex Oromucosal Spray UK/H/961/01/DC; pp. 1-46; 2016; www.mhra.gov.uk/con 2033.

Whittle, et al; Prospects for New Cannabis-Based Prescription Medicines; Journal of Cannabis Therapeutics vol. 1, No. 3/4, 2001 pp. 183-205.

USP 39, Physical Tests, Section 601 Inhalation and Nasal Drug Products, pp. 423-449, official from May 1, 2016; The United States Pharmacopoeia.

Guidance for State Medical Cannabis Testing Programs; Association of Public Health Laboratories; May 2016 https://www.aphl.org/aboutAPHL/publications/Documents/EH-Guide-State-Med-Cannabis-052016.pdf.

Takeda, Shuso, et al;, Cannabidiolic Acid as a Selective Cyclooxygenase-2-Inhibitory Component in Cannabis; Drug Metabolism and Disposition, vol. 36, No. 9, 1917-1924, 2008.

Scott, Katerine Ann, et al; Enhancing the Activity of Cannabbidiol and other Cannabinoids in Vitro Through Modifications to Drug Combinations and Treatment Schedules; Anticancer Research, 33, 4373-4380 (2013).

Acidic versus Activated Cannabinoids—Tips on How to Choose the Therapy Regimen that is Right for You; http://pureanalytics.net/blog/2012/05/09/acidic-versus-activated-cannabinoids-tips-on-how-to-choose-the-therapy-regimen-that-is-right-for-you/.

* cited by examiner

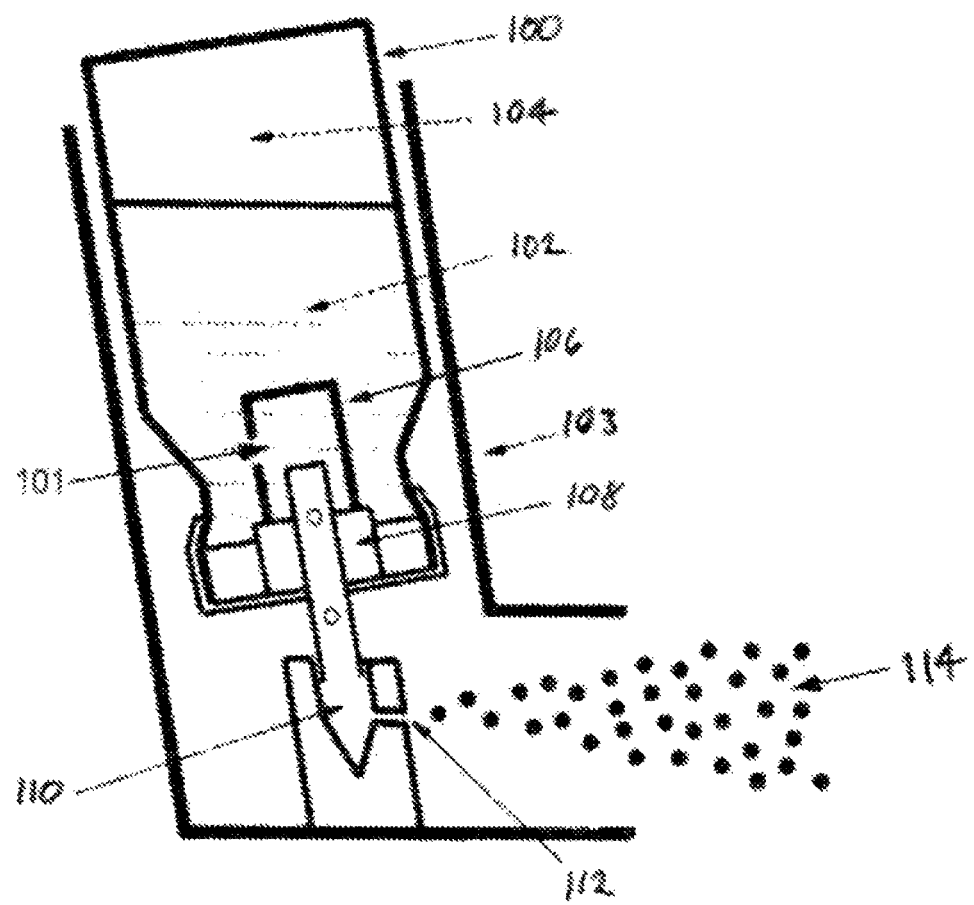

LOW-TEMPERATURE INHALATION ADMINISTRATION OF CANNABINOID ENTITIES

CROSS-REFERENCE TO RELATED APPLICATIONS

Not Applicable.

STATEMENT REGARDING FEDERALLY SPONSORED RESEARCH OR DEVELOPMENT

Not Applicable

Field of the Invention

The present invention is directed to the field of cannabinoid plant extracts and cannabinoid active agents, especially to cannabidiol (CBD), cannabidiolic acid (CBD Acid), tetrahydrocannabinol (THC), tetrahydrocannabinolic acid (THC Acid), tetrahydrocannabivarin (THCV), tetrahydrocannabivarinic acid (THCV Acid), cannabinol (CBN), cannabinolic acid (CBN Acid), cannabigerol, and cannabigerolic acid as active agents. The invention also relates to the field of formulations of these materials for inhalation therapy, as well as to the field of inhalation therapeutic therapies.

Background of the Invention

The field of therapeutic use of cannabinoid active agents has blossomed in recent decades as the therapeutic use of cannabinoids has become legalized in more and more jurisdictions. Most uses of cannabinoids, whether as whole plant, extracts of the plants, and as purified compounds (natural or synthetic), has been primarily in the direction of (a) ingesting the materials orally either as solid oral dosage forms or by means of being baked into various orally ingestible baked goods, (b) delivery to the lungs by virtue of (1) smoking cannabinoid containing plant parts, or (2) vaporizing extracts (partially or highly purified compounds)—whether solid or liquid—via the application of heat in order to vaporize the cannabinoid containing substance. While these methods of administration do deliver active principles, each of these methods suffer from various defects and problems. For example, one problem is the fact that the application of heat to cannabinoids changes the composition of the plant cannabinoids in significant part from for example cannabinoid acids to corresponding non-acid cannabinoids. In the case of THC (tetrahydrocannabinol), the structurally different acid version of the material (tetrahydrocannabinolic acid) is substantially less psychotropic than the tetrahydrocannabinol itself. Thus, application of heat, either during the process of extraction or in the course of delivery by smoking the material or in the use of vaporizers, increases the psychoactive effects, In the case of CBD (cannabidiol) and the acid forms of the other cannabinoids, which are not psychotropic, the structurally different acid version of the material (cannabidiolic acid et cetera) has shown increased in vivo activity compared to the cannabidiol itself and the corresponding non-acid forms of the other cannabinoids, respectively. Thus, the application of heat, either during the process of extraction or in the course of smoking the material or in the use of vaporizers, modifies the in-vivo effects. In both cases, the acid form of the material is the precursor of the corresponding decarboxylated material. As the therapeutic uses of cannabinoids are directed to activities other than the psychoactive effects, the use of smoking and vaporizing as delivery methods are disadvantageous. In addition, oral ingestion modes of administration, including sublingual administration, require significant doses in order to obtain the desired effects due to a very high first pass metabolism effect of cannabinoids. Thus, administration methods that can avoid the first pass metabolism effect would be desirable as allowing for reduction in dosage amounts needed to obtain desired effects.

Objects of the Invention

It is among the objects of the present invention to provide a formulation of cannabinoid active principles that can avoid the first pass metabolism effects associated with oral delivery or ingestion, including sublingual delivery.

It is another object of the invention to provide a formulation of extracts of cannabinoid containing plant parts, the extracts containing cannabinoid active principles that can be administered in suitable doses without the use of heating above 50° C.

It is another object of the invention to provide a formulation of synthetic or semi-synthetic cannabinoids that can be administered in suitable doses without the use of heating above 50° C.

It is yet another object of the invention to provide an extraction procedure of cannabinoid material containing plant parts, in which the extracts are obtained without the use of heating above 50° C.

It is still another object of the invention to provide an inhalation suitable formulation of one or more cannabinoid active principles.

It is still another object of the invention to provide an inhalation suitable formulation of one or more cannabinoid active principles capable of being delivered to a subject in microdoses.

Yet a further object of the invention is to provide an inhalation suitable formulation of one or more extracts of a cannabinoid containing plant.

Still a further object of the invention is to provide an inhalation suitable formulation of one or more cannabinoid containing active principles where such formulation has as a principle solvent, a pharmaceutically acceptable propellant, with or without a pharmaceutically and inhalation suitable co-solvent.

An even further object of the invention is to provide a metered dose inhalation suitable formulation containing one or more cannabinoid active principles.

Yet an even further object of the invention is to provide a metered dose inhaler system for delivery of the foregoing cannabinoid containing formulations of the previous object of the invention.

Still an even further object of the invention is to provide a method of treatment of a cannabinoid active principle responsive condition via administration of an inhalation suitable formulation of the cannabinoid active principle without the use of the application of heat over 50° C. and without the use of burning.

Yet another object of the invention is to provide a metered dose inhaler that delivers one or more formulations of the previous objects of the invention in therapeutically effective amounts for one or more of the various cannabinoid responsive conditions, which therapeutically effective amount is substantially reduced relative to the dose needed for oral or sublingual administration thereof.

Still another object of the invention is to provide a method of treatment of a cannabinoid responsive condition with substantially reduced psychoactive effects relative to administration by smoking or by vaporizing and at a substantially reduced therapeutically active dosage as compared to oral administration, sublingual administration, or topical administrations Still other objects of the invention will be recognized by those of ordinary skill in the art.

Brief Summary of the Invention

These and other objects of the invention are surprisingly achieved by a formulation of (1) a cannabinoid material selected from the group consisting of (a) an extract of a cannabinoid containing plant part, (b) a cannabinoid active principle in partially or completely purified form, (c) a synthetic cannabinoid, or (d) a combination thereof; dissolved in one or more pharmaceutically and inhalation acceptable propellant(s), optionally in the presence of one or more pharmaceutically and inhalation acceptable co-solvent(s) for the cannabinoid material(s); which formulation is delivered via a metered dose inhaler device without the need for heating over 50° C. during delivery.

BRIEF DESCRIPTION OF THE DRAWING

FIG. 1 is a partial cross-sectional view of a metered dose inhaler generally known in the art.

DETAILED DESCRIPTION OF THE INVENTION

The present invention is a formulation of (1) a cannabinoid material selected from the group consisting of (a) an extract of a cannabinoid containing plant part, (b) a cannabinoid active principle in partially or completely purified form, (c) a synthetic cannabinoid material, (d) mixtures of synthetic cannabinoids or (e) a combination thereof; dissolved in one or more pharmaceutically and inhalation acceptable propellant(s), optionally in the presence of one or more pharmaceutically and inhalation acceptable co-solvent(s) for the cannabinoid material(s); which formulation is delivered via a metered dose inhaler device without the need for heating over 50° C. during delivery and in the absence of heating over 50° C. during delivery. For purposes of this specification cannabinoid compounds are defined to include without limitation, those having any one of the structures I-IX below:

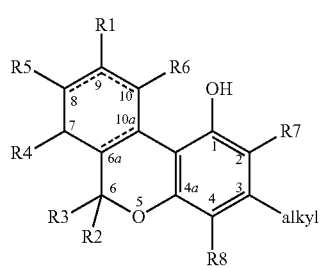

Formula I

Tetrahydrocannabinol-type
and
Cannabinol-type

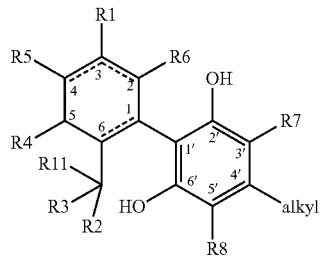

Formula II

Cannabidiol-type

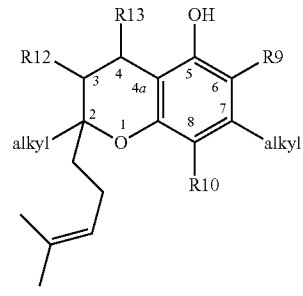

Formula III

Cannabichromene-type

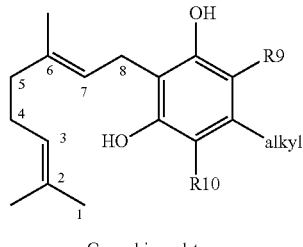

Formula IV

Cannabigerol-type

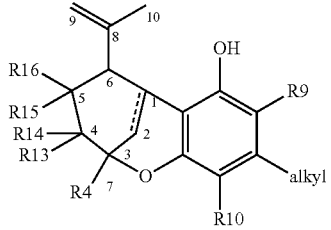

Formula V iso-Tetrahydrocannabinol-type

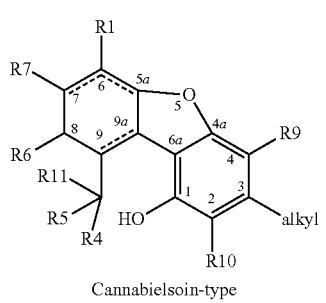

Formula VI

Cannabielsoin-type

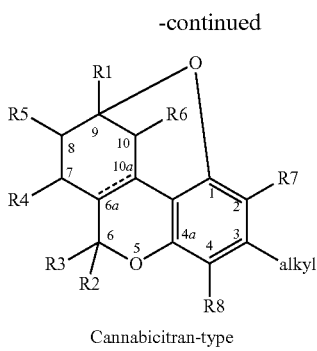

Formula VII

Cannabicitran-type

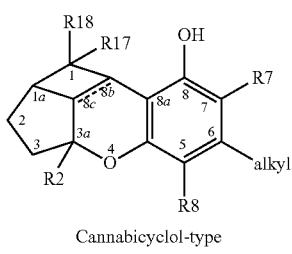

Formula VIII

Cannabicyclol-type

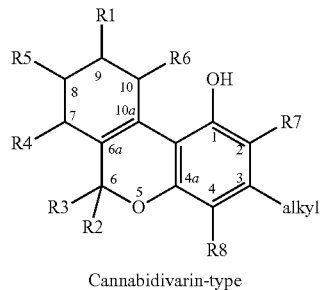

Formula IX

Cannabidivarin-type wherein R1 is lower alkyl, —CH₂(OH)lower alkyl, —CHO, —C(=O)lower alkyl, or —COOH or a ester or amide or salt of —COOH or an ester or salt of the alcoholic OHs, the complementary groups forming the esters and amides being pharmaceutically acceptable and preferably being lower alkyl (for esters with acidic functions in the structures shown) and mono- di- and tri-lower alkylamines (for amides with acidic functions m the structures shown) and lower alkylcarbonyl (for hydroxy functions in the structures shown);

R2 and R3 are independently H, lower alkyl, or together are =CH₂, or =CH-lower alkyl, or =C (lower alkyl)(lower alkyl);

R4 is H or lower alkyl;

R5 and R6 are independently H or lower alkyl;

R7-R10 are independently H, lower alkyl, —CH₂OH, —CHO, —COOH, or an ester or amide or salt thereof, the group completing the ester or amide or salt being independently selected from the same moieties as described above;

R11-R16 independently being H, or lower alkyl;

all recitations of "alkyl" without specific carbon length or modified by "lower" being C1-C10 in length; and all recitations of "alkyl" and "lower alkyl" being understood as being straight chain or branched chain. "Cannabinoid" compounds as used herein further includes each of the specifically named cannabinoids that are recited above or below.

Preferably the cannabinoid material is selected from any of the known cannabinoids. These include, without limitation, tetrahydrocanabinols (including without limitation Δ9 tetrahydrocannabinol and its isomers, especially, including without limitation, trans (−)-Δ9 tetrahydrocannabinol, and trans (+)-Δ9 tetrahydrocannabinol) and their isomers, tetrahydrocannabinolic acids (including without limitation Δ9 tetrahydrocannabinolic acid, and its isomers, especially, including without limitation, trans (−)-Δ9 tetrahydrocannabinolic acid, and trans (+)-Δ9 tetrahydrocannabinolic acid and their isomers) cannabidiol, cannabidiolic acid, cannabigerolic acid, cannabigerol, cannabigerovarinic acid, cannabigerolovarin, cannabichromenic acid, cannabichromene, cannabidivarin, cannabidivarinic acid, cannabivarin, cannabivarinic acid, tetrahydrocannabivarinic acid, tetrahydrocannabivarin, cannabinolic acid, cannabinol, cannabinodiol, cannabielsoin, cannabicyclol, and cannabicitran and isomers thereof, and various mixtures thereof. The foregoing cannabinoids further include the corresponding acid variations of any of the specifically mentioned non-acid variants. Preferably the major component of a mixture of cannabinoids is selected from one or more of Δ9 tetrahydrocannabinol, Δ9 tetrahydrocannabinolic acid, cannabidiol, cannabidiol acid, cannabichromic acid, cannabichromene, cannabigerolic acid, cannabidivarin, cannabivarinic acid tetrahydrocannabivarinic acid, tetrahydrocannabivarin and cannabigerol, Even more preferably, the cannabinoid material is one or two cannabinoid pairs selected from tetrahydrocannabinol (preferably a Δ9 tetrahydrocannabinol)/tetrahydrocannabinolic acid (preferably a Δ9 tetrahydrocannabinolic acid) and cannabidiol/cannabidiolic acid, which may have "very small amounts" of additional cannabinoids as well, the "very small amounts" being a weight/weight % of not greater than 20% (more preferably not greater than 10%, still more preferably not greater than 5%) relative to the total cannabinoid content of the formulation. When more than one major cannabinoid material is present, the total major cannabinoid materials can be present at 80-100 wt/wt % of the total cannabinoid materials content of the formulation. In other preferred embodiments, the major cannabinoid materials are substantially all acid variant forms; in some even more preferable embodiments, all of the cannabinoid materials in the formulation are acid variant forms. In still other embodiments, the major cannabinoids are CBD alone or with one or more cannabinoid acids. Unless, "cannabinoid acid" is specifically being distinguished from "non-acid cannabinoid" in this specification, the term "cannabinoid" without the qualifier "acid" is deemed to include both the cannabinoid acid forms and the cannabinoid non acid forms.

The cannabinoid, whether extract, partially purified cannabinoid, or highly purified cannabinoid or mixture thereof, can be dissolved in either the pharmaceutically acceptable, inhalation acceptable propellant alone or first dissolved in a small amount of pharmaceutically acceptable, inhalation acceptable co-solvent. Where concentrations above the solubility of the cannabinoid components in the propellant are desired, the co-solvent can be added to obtain higher concentrations of these materials without the use of heat above the temperatures indicated elsewhere in this specification and in any event without the use of heating the material beyond 50° C. or more preferably without heating the material beyond the more preferred temperatures specified below in this paragraph. The pharmaceutically acceptable, inhalation acceptable co-solvent is selected from, without limitation, ethanol, propanol, propylene glycol, glycerol, polyethylene glycol (preferably without limitation PEG 300 or PEG 400), or mixtures thereof, preferably selected from ethanol, propanol, propylene glycol, glycerol, more preferably ethanol. When used, the co-solvent is present in an amount of from about 0.05%, up to 30% based on the total of the propellant and co-solvent, more preferably, the cosolvent is present in ranges having a lower limit selected from 0.05%, 0.06%, 0.07%, 0.08%, 0.09%, 0.1%, 0.15%, 0.2%, 0.25%, 0.30%, 0.35%, 0.40%, 0.45%, 0.5%, 0.55%, 0.6%, 0.65%, 0.70%, 0.75%, 0.8%, 0.85%, 0.9%, 0.95%, 1%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.25%, 3.5%, 3.75%, 4.0%, 4.25%, 4.5%, and 5.0%, an upper limit selected from 0.5%, 0.55%, 0.6%, 0.65%, 0.70%, 0.75%, 0.8%, 0.85%, 0.9%, 0.95%, 1%, 1.1%, 1.2%, 1.3%, 1.4%, 1.5%, 1.6%, 1.7%, 1.8%, 1.9%, 2.0%, 2.1%, 2.2%, 2.3%, 2.4%, 2/5%, 2.6%, 2.7%, 2.8%, 2.9%, 3.0%, 3.25%, 3.5%, 3.75%, 4.0%, 4.25%, 4.5%, 4.75%, 5.0%, 10%, 15%, 20%, 25%, and 30% provided that the particular upper limit selected is greater than the particular lower limit selected, each range being the amount of co-solvent relative to the combination of co-solvent and propellant, each % being weight/weight %. In addition to being a co-solvent, the co-solvent may be suitably used to remove various insoluble contaminants before adding the pharmaceutically acceptable, inhalation acceptable propellant. In such situation, the cannabinoid material can be dissolved in the co-solvent, and the solution is filtered to remove any non-solubilized components and the filtered solution is then utilized. The filtration procedure can occur at room temperature or after cooling of the ethanol solution. If desired, mild heating can be used in the dissolution process, but is not to exceed a temperature selected from 50° C., 45° C., 40° C., 35° C., and 30° C., preferably without raising the temperature above a temperature selected from 40° C., 35° C., and 30° C., most preferably without the application of heat at all. (If it is desired to remove the particular co-solvent above after the filtration, such removal can be done under the same conditions set forth below for the solvents that are not inhalation compatible.) Alternatively, if it is desired, for insoluble material removal, to use a solvent that is not acceptable for inhalation or is not compatible with the propellant, such solvent may be used to dissolve the cannabinoid material, filter out any non-solubles, and then remove the inhalation unacceptable solvent without the application of heat that would cause conversion of any of the present cannabinoids into another cannabinoid. Thus, vacuum evaporation without any heating or without raising the temperature above a temperature selected from 50° C., 45° C., 40° C., 35° C., or 30° C., preferably without raising the temperature above a temperature selected front 40° C., 35° C., or 30° C., most preferably without the application of heat at all can be used. Suitable solvents that are not both inhalation acceptable and non-interactive with the propellant for this "purification" aspect are limited to those that can be removed suitably under these conditions. Such solvents that are either or both not inhalation acceptable and/or are incompatible with the propellant and suitable as per the above limitations include, but are not limited to, butane, pentane, hexanes, heptanes, diethyl ether, ethyl acetate, methylene chloride, chloroform, acetone and mixtures thereof is particularly preferred. Where mixtures of solvents are desired to be used for the removal of the insolubles, such mixtures can be of the "co-solvents", mixtures of the "non-cosolvent solvents" or mixtures of both, provided that if any non-cosolvent solvent is used, at least all of the non-cosolvent solvents must be removed before further formulation.

Propellants for the present invention are the pharmaceutically acceptable, inhalation acceptable hydrofluoroalkanes (HFAs). These include, but are not limited to, HFA 134a (tetrafluoroethane) HFA 227 (heptafluoropropane) and mixtures thereof; HFA 134a and HFA 227 being readily available in the marketplace from Mexichem Fluor, Inc. The propellants comprise the bulk of the present formulations, typically in the range of from 50% wt/wt to 99.5% wt/wt, preferably in the range from 60% to 99%, more preferably in the range 80 to 99% and most preferably in the range of 90% wt/wt to 99% wt/wt. Usually, the formulation comprises the active materials, the propellant and optionally the co-solvent, preferably consists essentially of the active materials, the propellant and optionally the co-solvent, still more preferably the formulation consists of the active materials, the propellant and optionally the co-solvent.

For example, in the case of a 100 ul metered dose inhaler valve, the delivered dose amount (from the metered dose inhaler unit) of cannabinoid material present in the formulation is from 0.01 mg to 20 mg per 100 ul actuation of formulation (where the shot weight of the emitted volume (100 ul) of formulation would range from 80 mg to 140 mg depending upon the presence of (and the particular) co-solvent and the particular HFA used at 20° C. (for example using 100% HFA 227 and active agent, the shot weight of 100 ul of formulation is about 140 mg). preferably in a range, per 100 ul of formulation, selected from those having a lower limit selected from 0.01 mg, 0.02 mg, 0.025 mg, 0.03 mg, 0.04 mg, 0.05 mg, 0.06 mg, 0.07 mg, 0.075 mg, 0.08 mg, 0.09 mg, 0.1 mg, 0.25 mg, 0.5 mg, 1 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.54 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.25 mg, 4.5 mg, 4.75 mg, and 5.0 mg, and an upper limit selected from 1.0 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.25 mg, 4.5 mg, 4.75 mg, 5.0 mg, 10 mg, 15 mg, and 20 mg provided that the selected upper limit is greater than the selected lower limit. A highly preferred concentration of the cannabinoid material in the formulation are selected from those above having a lower limit of at least 0.25 mg/100 ul of formulation and an upper limit of not more than 10 mg/100 ul of formulation. Actual dosage is a function of the concentration of the actives in the formulation and the volume emitted by the device and the respirable fraction. Appropriate adjustments in the size (volume of formulation emitted) of the valve, concentration of active material in the formulation, and respirable fraction (which can be varied with (a) the diameter of the stem block nozzle opening in the metered dose inhaler, (b) the amount of co-solvent in the formulation, (c) the valve metering volume, all of which are well within the abilities of those of ordinary skill in the art having benefit of the present specification). For example, if the respirable fraction for a particular formulation is too low (i.e., dosage reaching the lungs is not sufficient), it can be increased by making the actuator orifice diameter opening smaller, or reducing the co-solvent concentration (if possible), or adjusting the valve size to a smaller metering volume. If the respirable fraction is too high, one can adjust these same parameters in the opposite direction. Since these adjustments interplay with and affect one another, it is typical to construct a suitable device, test it for consistency between manufacturing lots, determine the dose delivered by the device, and determine the particle size of the emergent droplets and the fraction of the dose reaching the lungs. Thereafter, one adjusts one or more of the device or formulation parameters as mentioned above and re-determine the respirable dose being delivered to the lungs with the modified formulation/device. The process is repeated as needed until such time as the precise formulation concentration, and device parameters are such that an appropriate actual dose (or suitable surrogate therefor) is determined. Such testing as set forth herein, while not insignificant, is not undue experimentation, is well within the abilities of those of ordinary skill in the art having benefit of the present specification, and is generally required by regulatory agency approval of the pharmaceutical product which includes both the metered dose inhaler package (canister, valve and actuator) and the formulation delivered thereby.

Non-limiting, typical properties of cannabinoids known in the art and include, without limitation, antibiotic, antifungal, antiinflammatory, analgesic, anxiolytic, antipsychotic, antioxidant, antispasmodic, antiemtic, sedative, anorectic, antidiabetic, antidepressant, antiepileptic, antiinsomnia, antiischemic, antiproliferative, antiosioratic, antipsychotic, anxiolitic, appetite stimulant, bone stimulant, anti-cancer, and the formulations of the present invention may be used to treat one or more thereof. Suitable closings emitted from the inhaler used in the present CBD based formulations to deliver adequate therapeutic amounts would require a delivery of about 0.02 to 20 mg of active principles about every 8 to 12 hours, which is conveniently obtained by a metered dose inhaler delivering about 0.01 to 5 mg of active principles/spray with about 2-4 sprays per dose every 8-12 hours provided the dose of active is suitably and efficiently (30% or more respirable fraction as determined by Cascade Impaction) delivered into the lungs. In other words, a total daily dose of the active principles would be (0.02 to 20 mg per dosing)×(2-3 times a day)×(30% respirable fraction or more)=0.012 mg/day (based on a 30% respirable fraction and twice daily dosing) at the low end to 18 mg/day (based on a 30% respirable fraction and three times a day dosing) at the higher end; 0.02 mg/day (based on a 50% respirable fraction and twice daily dosing) at the low end to 30 mg/day (based on a 50% respirable fraction and three times a day dosing) at the high end, daily doses at a theoretical 100% respirable fractions being 0.04 mg/day to 60 mg/day.

Metered Dose inhalers of various design are generally available on the market However, not all available metered dose inhalers suitably deliver the active substantially to the lungs, with a substantial portion being lost to the oral mucosa and the tongue. In situations where the first pass metabolism is not great, such a result may not play a significant role. However, in the present invention, substantial losses to the oral mucosa will substantially affect the results achieved. Thus, it may be necessary to conduct a certain degree of experimentation with existing metered dose inhaler components or construct modifications thereof based on the results of such experimentation so as to meet target specific demands. The components referred to are the formulation (as described above), the container, the metering valve, and the actuator device. A typical metered dose inhaler of the art is shown in FIG. 1. FIG. 1 illustrates a canister 100 used to contain and aerosolize a liquid formulation 102 of the present disclosure. The canister 100 is received within a stem block cavity in an actuator 103, or inhaler. The liquid formulation 102 substantially fills a retaining cup 106 positioned in the valve of the canister 100. A propellant 104 is used in the formulation by forming liquified propellant, a major part of the liquid formulation 102. When the canister 100 is pushed downward within the actuator 103, a metering chamber 108, in the valve which contains a spring releases a precise, predetermined amount of the liquid formulation 102. The released liquid formulation 102 enters the expansion chamber 110 where the liquid formulation 102 is released and expands. The formulation 102 then exits an actuator mouthpiece 112 firming an aerosolizing formulation 114. The aerosolized formulation 114 is formed of droplets or particles measuring between one (1) and five (5) micrometers in diameter, for example, 2 micrometers to 3 micrometers in diameter.

In use, a user can place their mouth over the exit of the actuator 103, press the canister 100 downward against the valve/actuator 103 and inhale deeply to carry the aerosolized formulation cloud 114 into the alveoli of the lungs, where active ingredients in the aerosolized formulation 114 are deposited or absorbed rapidly into the blood stream, resulting in a faster perceived benefit of effect of the active ingredient while simultaneously bypassing first pass liver metabolism associated with oral drug delivery.

The pharmaceutical solution formulations in hydrofluoroalkanes (HFAs) used in the present invention are filled into canisters suitable for delivering pharmaceutical aerosol formulations. Canisters for use in metered dose inhalers in the preset invention generally comprise containers capable of withstanding the vapor pressure of the HFA propellant, such as plastic, or plastic coated glass bottles or preferably a metal can, for example a stainless steel or aluminum can which is preferably anodized, organic coated and/or plastic coated. Generally suitable materials can be found in the disclosures of WO/2015/195711, and WO/2015/200049, both of which are incorporated by reference with respect to suitable materials for metered dose inhaler components. In the event of a formulation incompatibility with a particular container, one of the alternative containers above should be tried, preferably plastic coated containers or anodized aluminum, stainless steel or glass. The container is sealed with a metering valve, the metering valve comprising a metering chamber is designed to deliver a metered amount of the formulation per actuation and incorporates a gasket to prevent leakage of propellant through the valve. The gasket may comprise any suitable elastomeric material such as for example low density polyethylene, chlorobutyl, black and white butadiene acrylonitrile rubbers, butyl rubber, and neoprene. A valve stem extends from the metering valve and acts as a conduit to pass the metered dose into a nozzle block situated in the actuator body in which the valve stem is inserted Suitable valves are commercially available from manufacturers well known to the industry.

Each filled canister is fitted into a suitable channeled device (actuator) prior to use to form a metered dose inhaler package for administration of the medicament into the lungs or nasal cavity, preferably into the lungs, of a patient. In a typical arrangement, the valve stem is seated into a nozzle stem block which comprises an actuator orifice leading then to an expansion chamber/mouthpiece. This expansion chamber/mouthpiece is how the patient interacts with the inhaler device to inhale the dose emitted upon actuation of the device. Conventional HFA actuators have variable actuator orifice diameters ranging from 0.1 to 0.6 mm. The choice of actuator orifice size is decided primarily by the formulation ingredients, the physical properties of the formulation and the lung or nasal target areas. The goal of this choke is to deliver highly respirable doses (at least 30%, preferably at least 35%, more preferable at least 40%, still more preferable, at least 45%, most preferably at least 50%) capable of reaching the lung (without significant losses to the actuator, valve, canister, the oral cavity, and by exhalation).

This selection effort requires significant testing of the deliver characteristics of the chosen package (actuator, valve, canister) with the specific test formulation. While not all of these tests are relevant for the determination of a suitable metered dose inhaler, many of the tests for product uniformity and reliability of the respirable fraction set forth in the United States Pharmacopeia (USP) 39, official from May 1, 2016, Physical Tests (601) Inhalation and Nasal Products, p. 423-449 Chapter on Physical Tests and Determinations (incorporated herein by reference), are useful for the determination of whether a particular formulation in conjunction with a particular metered dose inhaler will meet the limitations of the present invention. Once tested to obtain the particular results of a particular formulation used with a particular metered dose inhaler, those of ordinary skill in the art will be able to adjust active agent concentration, the concentration or presence of any co-solvent, actuator design, and jet orifice diameter in order to achieve the appropriate combination of concentration, volume of delivery of formulation per actuation, and respirable fraction so as to achieve the desired dosages as set forth herein. Where a single actuation is insufficient to deliver the full dose target, multiple actuations can be used at a particular dosing point in order to achieve a suitable total dose.

As stated above, the overall objective of the present invention is to achieve a therapeutically effective amount of active agent(s) to the lung with a minimal amount of losses to the oral cavity and metered dose inhaler components. This allows for the elimination of excessively large doses that might otherwise be needed in order to achieve the desired therapeutically effective amount where losses to the oral cavity are significant (which may give rise to undesirable side effects). It should be noted that the following tests are not limitations on the invention but are merely a convenience for testing product to determine whether particular devices and formulations when used in combination will result in a method, combination (device with the formulation), or treatment within the scope of one or more claims of the present invention.

Where the various in vitro tests are detailed in the USP (USP 39, chapter 601), those tests and testing equipment is the preferred method of testing. It is recognized that the USP allows for a number of variations in the testing, but since the ultimate key result is a respirable fraction (for example at least 30%) of a particular amount of active agent reproducibly delivered by the metered dose inhaler utilizing a particular formulation is what is important, the precise manner of obtaining these values is described in a validated test method developed for the specific product. The important aspect is that one knows how much of the active agent mass is delivered out of the metered dose inhaler per actuation and what fraction of that amount is delivered in a manner that is actually deposited in the lungs of a user. Some tests specified by the USP are for testing of product uniformity, metered dose inhaler to metered dose inhaler, some are for testing metered dose inhaler consistency of delivered amount per actuation. These are performed to assure that the reliability of the metered dose inhaler unit used is properly working so that the remaining test results can be relied upon. Other tests are directed to determination of the respirable dose itself, which is important to the value of the present invention in reducing the amount of cannabinoid active agent needed to be used per target dose to obtain a specific treatment effective amount.

The various tests one of ordinary skill in the art may use that are in the USP or that are in addition to those in the USP, or that are alternatives to those in the USP but only after a correlation between the USP test and the alternative has been appropriately validated include, but are not limited to:

1. Spray actuation content uniformity thru the life of the unit (beginning, middle and end stages of use) (testing reliability of the metered dose inhaler unit being used). This test is detailed in USP 39, chapter 601 and should be conducted in accordance therewith.
2. Fine particle dose and fine particle fraction (respirable fraction) thru the life of the unit by Cascade impaction technologies (determination of the respirable fraction). This test is detailed in USP 39, chapter 601 and should be conducted in accordance therewith.

At such time as a product of the present invention is available on the market, samples of such product should be tested in any specific protocol as a confirmation that the specific protocol being used is valid by resulting in the measured respirable fraction within the claim limits of the present application and then such specific protocol testing repeated with a proposed alternative product when one wishes to determine if a proposed alternative product is within the invention or not.

Once testing above is completed and the respirable fraction determined, the dosage per actuation actually reaching the lung is estimated by multiplying the dose per actuation delivered (by the metered dose inhaler) by the respirable fraction. In cases where this is too small for the desired dosing, one of ordinary skill adjusts concentration of the active, the actuator design, the stem block jet orifice opening diameter or combination of one or more of the above and retests the modified formulation with the modified metered dose inhaler, or the original formulation with the modified metered dose inhaler or any combination thereof as appropriate. Based on those test results, the process may be repeated or not as desired until the various parameters are optimized to give a desired delivered dose of a formulation of the cannabinoid to the lungs of the subject being treated.

EXAMPLES

The following examples exemplify, but do not limit, the present invention,

Example 1

A formulation is prepared as set forth below.

| | | |
|---|---|---|
| CBD (98% pure powder)- | 97 mg = | 1.55% |
| Ethanol-- | 200 mg = | 3.19% |
| HFA 134a | 5970 mg = | 95.23% |
| SubTotal | 6267 mg = | 99.97 |
| Impurities in CBD | 2 mg = | 0.03% |
| Total | 6269 mg = | 100.00% |

The formulation is prepared as follows;
98% CBD powder (99 mg) is weighed out and transferred to a suitable container and ethanol (0.2 g) added till solution is observed. The solution is transferred to an appropriate aerosol container (glass, aluminum) and a metered dose inhaler valve (100 ul) crimped on. The sample is then pressure filled with 5.97 g HFA 134a. The final product is a yellow solution. This formulation will deliver about 2.0 mg of CBD per actuation.

Example 2

Following the procedure in example 1 except that the particular components and amounts are selected as shown in the table below, formulations of the present invention are prepared:

| Example | Cannabinoid (98% CBD) g | g/100 ul | Cosolvent (ethanol) g | % w/w of formulation | Propellant (HFA134a) g | % w/w of formulation |
|---|---|---|---|---|---|---|
| 2a | 0.0504 | 0.64 | 0.2 | 2.1 | 9.37 | 97.40 |
| 2b | 0.0265 | 0.37 | 0.366 | 4.13 | 8.48 | 95.58 |
| 2c | 0.098 | 0.099 | 0.410 | 4.2 | 9.25 | 94.80 |

Example 3

Following the procedure in example 1 except that the particular components and amounts are selected as shown in the table below and the starting material is a 24% CBD enriched cannabinoid extract, a formulation of the present invention is prepared:

| Example | Cannabinoid (98% CBD) oil in g | mg/100 ul | Cosolvent (ethanol) g | % w/w of formulation | Propellant (HFA134a) g | % w/w of formulation |
|---|---|---|---|---|---|---|
| 1 | 0.5117 | 2.0 | 1.18 | 15.63 | 4.8 | 82.74 |

The formulation is prepared as follows;
Cannabinoid extract oil enriched in 24% CBD (0.5117 g of oil) is weighed out and transferred to a suitable container and ethanol (1.18 g) added. The resulting solution contained some insoluble particles which were remove by filtration. It was determined that during filtration, 23% of the weight was lost. The filtered solution is transferred to an appropriate aerosol container (glass, aluminum) and a metered dose inhaler valve (100 ul) crimped on. The sample is then pressure filled with 4.81 g HFA 134a. The final product is a yellow solution. This formulation would deliver 2.0 mg of CBD per actuation.

We claim:
1. A formulation comprising:
   a cannabinoid material comprising at least one cannabinoid active agent, said cannabinoid material being an extract of a cannabinoid containing plant material;
   a hydrofluoroalkane (HFA) propellant;
   and a co-solvent for said cannabinoid active agent which consists of ethanol;
   said HFA propellant being present in an amount of from 50% by weight to 99.99% by weight based on the entire formulation;
   said co-solvent, being present in an amount of up to 21.05% by weight based on the entire formulation; and
   said cannabinoid material being present, in an amount based on the total of the two most predominantly present cannabinoid active agents of 0.01 mg/100 ul to 13.3 mg/100 ul of total formulation;
   wherein said extract contains from 1 up to 5 major cannabinoid pairs, each major cannabinoid pair consisting of the Acid and non-Acid forms thereof wherein to be considered a major cannabinoid pair, the cannabinoid pair must be at least 20% of the total cannabinoid content of the formulation, said major cannabinoid pairs being present collectively in an amount greater than 80% of the cannabinoids present in said extract,
   wherein each of said major cannabinoid pairs is present substantially in the acid form thereof;
   and
   wherein said extract is obtained in the absence of applying heat at all or in the absence of applying heat greater than 50° C.

2. The formulation of claim 1 wherein the co-solvent is present in an amount of from 0.1% by weight to 15% by weight based on the entire formulation.

3. The formulation of claim 1 wherein the propellant is selected from tetrafluoroethane (HFA 134a) and heptafluoropropane (HFA 227).

4. The formulation of claim 1 wherein the cannabinoid active agent is selected from the group consisting of a tetrahydrocannabinol (THC), a tetrahydrocannabinolic acid (THC Acid), cannabidiol (CBD), cannabidiolic acid (CBD Acid), cannabigerolic acid, cannabigerol, cannabigerovarinic acid, cannabigerolovarin, cannabichromenic acid, cannabichromene, cannabidivarin, cannabidivarinic acid, tetrahydrocannabivarinic acid, tetrahydrocannabivarin, cannabivarinic acid, cannabivarin, cannabinolic acid, cannabinol, and isomers thereof, and mixtures thereof.

5. The formulation of claim 4 wherein at least one of CBD and CBD Acid are present among the top five most predominantly present cannabinoid active agents in said formulation.

6. The formulation of claim 1 selected from the formulations indicated in the table below:

| | Cannabinoid (98% CBD) g | mg/100 ul | Cosolvent (ethanol) g | % w/w of formulation | Propellant (HFA134a) g | % w/w of formulation |
|---|---|---|---|---|---|---|
| Formulation 1 | 0.3 | 1.7 | 0.4 | 5.33 | 7 | 93.33 |
| Formulation 2 | 0.25 | 3.8 | 1.0 | 12.1 | 7 | 84.85 |

-continued

| | Cannabinoid | | Cosolvent | | Propellant | |
|---|---|---|---|---|---|---|
| | (98% CBD) g | mg/100 ul | (ethanol) g | % w/w of formulation | (HFA134a) g | % w/w of formulation |
| Formulation 3 | 0.5 | 6.8 | 2.0 | 21.05 | 7 | 73.68 |
| Formulation 4 | 1.0 | 11.24 | 4.0 | 20.0 | 7 | 70.0. |

7. A method of administration of a cannabinoid material comprising at least one cannabinoid active agent, to a subject, while substantially avoiding first-pass metabolism of said cannabinoid active agent associated with oral administrations of said cannabinoid material and avoiding heat associated chemical alteration of one or more of the active agent components of said formulation comprising administering the formulation of claim 1 to said subject via a metered dose inhalation delivery system (a) in the absence of any heating or (b) with heating to not more than 50° C.

8. The method of administration of claim 7 wherein said delivery system using said formulation delivers a shot weight with a respirable fraction of at least 30% w/w relative to the shot weight.

9. A method of treating a cannabinoid responsive condition in a subject in need thereof comprising delivering to said subject a cannabinoid material via the method of administration of claim 7.

10. A method of providing an effective therapeutic effect to a subject in need thereof of a cannabinoid acid from a formulation containing said cannabinoid acid and optionally one or more additional cannabinoid active agents comprising administering said cannabinoid acid, optionally together with said one or more other cannabinoid active agents via the method of claim 7, at a lower total daily dose of the total cannabinoid active agent content of said formulation relative to the total cannabinoid active agent daily dose needed to obtain the same effective therapeutic effect via each of an oral ingestion, sublingual administration, smoking, vaporizing, and topical administration of the same or different formulation having the same total cannabinoid acid and the same total cannabinoid active agent weight content.

11. The method of claim 10 wherein said method provides said effective therapeutic amount at a lower total dose than administration of the identical formulation via each of oral ingestion, smoking, or vaporized inhalation administration.

12. A method of treating a cannabinoid acid responsive condition in a subject in need thereof while substantially avoiding or substantially reducing psychotropic effects of cannabinoid non-acid forms comprising administering at least one cannabinoid acid compound, optionally together with another cannabinoid active agent in a formulation of claim 1 via a metered dose inhaler system wherein said effective amount of said cannabinoid acid is substantially reduced compared to oral ingestion, smoked, vaporized inhalation delivery, or topical administration of said cannabinoid acid, alone or optionally with said additional cannabinoid active agent respectively.

13. A formulation comprising:
a cannabinoid material comprising at least one cannabinoid active agent, said cannabinoid material being an extract of a cannabinoid containing plant material;
a hydrofluoroalkane (HFA) propellant;
and at least one co-solvent for said cannabinoid active agent which is selected from the group consisting of ethanol, propanol, isopropanol, propylene glycol, polyethylene glycol, and mixtures thereof;
said HFA propellant being present in an amount of from 50% by weight to 99.99% by weight based on the entire formulation;
said co-solvent, being present in an amount of up to 21.05% by weight based on the entire formulation; and
said cannabinoid material being present, in an amount based on the total of the two most predominantly present cannabinoid active agents of 0.01 mg/100 ul to 13.3 mg/100 ul of total formulation;
wherein said extract contains from 1 up to 5 major cannabinoid pairs, each major cannabinoid pair consisting of the Acid and non-Acid forms thereof, wherein to be considered a major cannabinoid pair, the cannabinoid pair must be at least 20% of the total cannabinoid content of the formulation, said major cannabinoid pairs being present collectively in an amount greater than 80% of the cannabinoids present in said extract, wherein each of said major cannabinoid pairs is present substantially in the acid form thereof; and
wherein said extract is obtained in the absence of applying heat at all or in the absence of applying heat greater than 50° C.

14. A method of administration of a cannabinoid material comprising at least one cannabinoid active agent, to a subject, while substantially avoiding first-pass metabolism of said cannabinoid active agent associated with oral administrations of said cannabinoid material and avoiding heat associated chemical alteration of one or more of the active agent components of said formulation comprising administering the formulation of claim 13 to said subject via a metered dose inhalation delivery system (a) in the absence of any heating or (b) with heating to not more than 50° C.

15. The method of administration of claim 14 wherein said delivery system using said formulation delivers a shot weight with a respirable fraction of at least 30% w/w relative to the shot weight.

16. A method of treating a cannabinoid responsive condition in a subject in need thereof comprising delivering to said subject a cannabinoid material via the method of administration of claim 14.

17. A method of providing an effective therapeutic effect to a subject in need thereof of a cannabinoid acid from a formulation containing said cannabinoid acid and optionally one or more additional cannabinoid active agents comprising administering said cannabinoid acid, optionally together with said one or more other cannabinoid active agents via the method of claim 14, at a lower total daily dose of the total cannabinoid active agent content of said formulation relative to the total cannabinoid active agent daily dose needed to obtain the same effective therapeutic effect via each of an oral ingestion, sublingual administration, smoking, vaporizing, and topical administration of the same or different formulation having the same total cannabinoid acid and the same total cannabinoid active agent weight content.

18. The method of claim 17 wherein said method provides said effective therapeutic amount at a lower total dose than administration of the identical formulation via each of oral ingestion, smoking, or vaporized inhalation administration.

19. A method of treating a cannabinoid acid responsive condition in a subject in need thereof while substantially avoiding or substantially reducing psychotropic effects of cannabinoid non-acid forms comprising administering at least one cannabinoid acid compound, optionally together with another cannabinoid active agent in a formulation of claim 13 via a metered dose inhaler system wherein said effective amount of said cannabinoid acid is substantially reduced compared to oral ingestion, smoked, vaporized inhalation delivery, or topical administration of said cannabinoid acid, alone or optionally with said additional cannabinoid active agent respectively.

* * * * *

UNITED STATES PATENT AND TRADEMARK OFFICE
CERTIFICATE OF CORRECTION

PATENT NO. : 9,717,683 B1
APPLICATION NO. : 15/196315
DATED : August 1, 2017
INVENTOR(S) : Eck et al.

Page 1 of 4

It is certified that error appears in the above-identified patent and that said Letters Patent is hereby corrected as shown below:

In the Specification

Column 3, Lines 55-63, the currently printed structure designated Formula I:

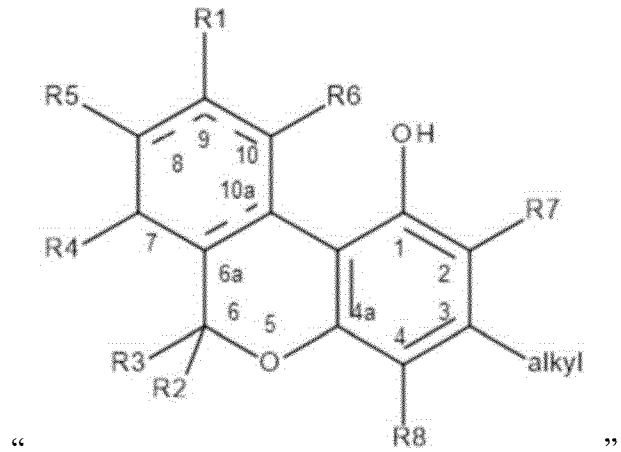

"

"

Should be replaced with:

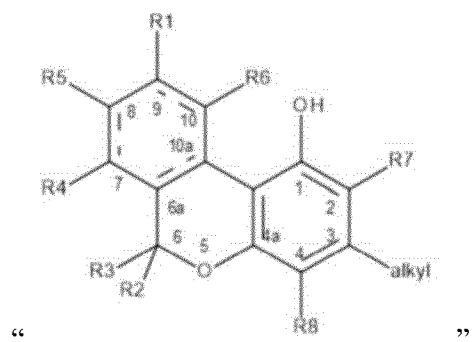

"

"

Signed and Sealed this
Ninth Day of June, 2020

Andrei Iancu
*Director of the United States Patent and Trademark Office*

CERTIFICATE OF CORRECTION (continued)
U.S. Pat. No. 9,717,683 B1

Column 4, Lines 2-13, the currently printed structure designated Formula II:

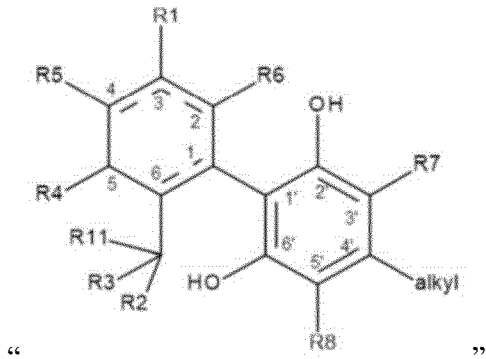

"

Should be replaced with:

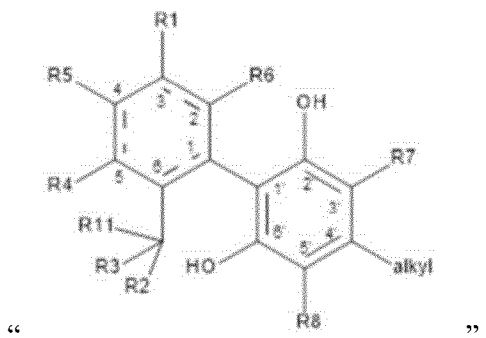

"

Column 4, Lines 15-26, the currently printed structure designated Formula III:

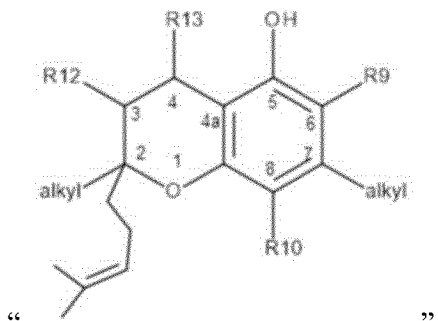

"

Should be replaced with:

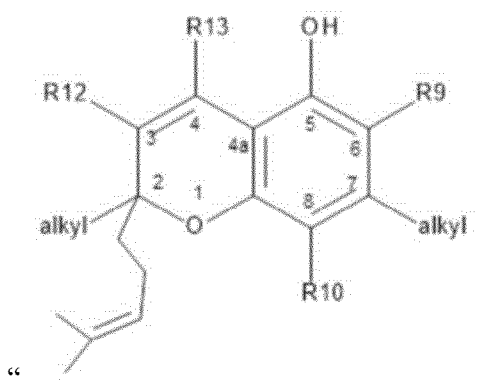

"

Column 4, Lines 41-50, the currently printed structure designated Formula V:

CERTIFICATE OF CORRECTION (continued)
U.S. Pat. No. 9,717,683 B1

Page 3 of 4

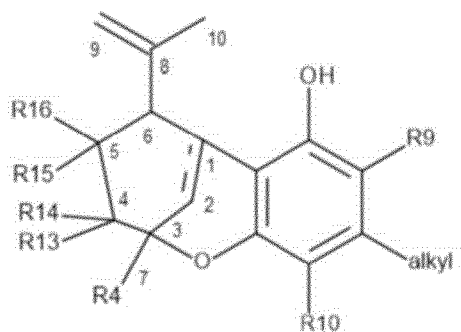

"                    "

Should be replaced with:

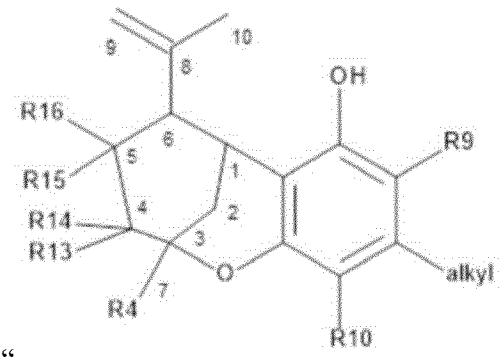

"                    "

Column 4, Lines 56-64, the currently printed structure designated Formula VI:

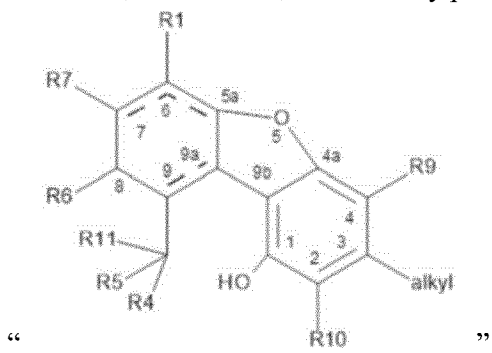

"                    "

Should be replaced with:

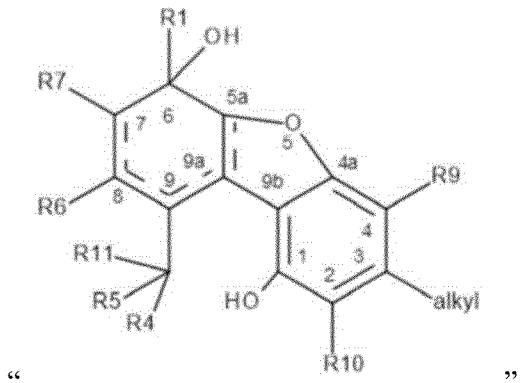

"                    "

Column 5, Lines 15-23, the currently printed structure designated Formula VIII:

CERTIFICATE OF CORRECTION (continued)
U.S. Pat. No. 9,717,683 B1

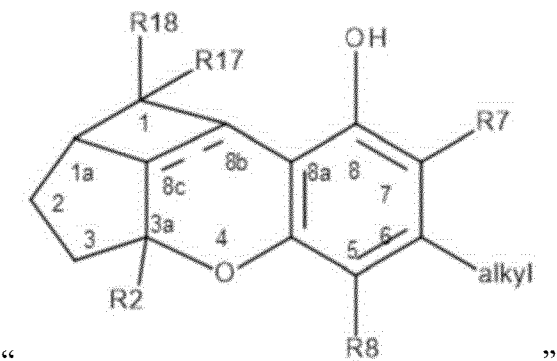

Should be replaced with:

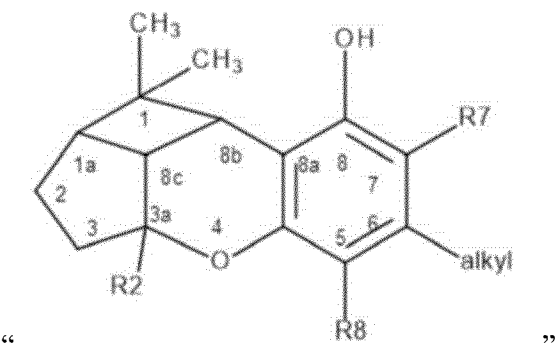

Column 5, Line 35 the currently printed designation "cannabidivarin" below the structure designated Formula IX should be replaced with "cannabivarin"

Column 5, Line 51, after "R5 and R6 are independently H or lower alkyl;" insert --and further with respect to Structural Formula VI that R4 and R5 may also together be CH2=--